(12) United States Patent
Chen et al.

(10) Patent No.: US 12,091,696 B2
(45) Date of Patent: Sep. 17, 2024

(54) O-METHYLTRANSFERASE PROTEIN WITH HIGHLY SPECIFIC CATALYTIC FUNCTION FOR MULTIPLE BIAS PARENT NUCLEI AND ENCODING GENE AND USE THEREOF

(71) Applicant: INSTITUTE OF CHINESE MATERIA MEDICA CHINA ACADEMY OF CHINESE MEDICAL SCIENCES, Beijing (CN)

(72) Inventors: Sha Chen, Beijing (CN); Yuetong Yu, Beijing (CN)

(73) Assignee: INSTITUTE OF CHINESE MATERIA MEDICA CHINA ACADEMY OF CHINESE MEDICAL SCIENCES, Beijing (CN)

( * ) Notice: Subject to any disclaimer, the term of this patent is extended or adjusted under 35 U.S.C. 154(b) by 0 days.

(21) Appl. No.: 18/447,649

(22) Filed: Aug. 10, 2023

(65) Prior Publication Data
US 2024/0052388 A1   Feb. 15, 2024

(51) Int. Cl.
| | |
|---|---|
| *C12P 17/12* | (2006.01) |
| *C12N 1/20* | (2006.01) |
| *C12N 9/10* | (2006.01) |
| *C12N 15/52* | (2006.01) |
| *C12N 15/70* | (2006.01) |
| *C12P 13/02* | (2006.01) |
| *C12P 17/18* | (2006.01) |
| *C12R 1/19* | (2006.01) |

(52) U.S. Cl.
CPC ............... *C12P 17/12* (2013.01); *C12N 1/205* (2021.05); *C12N 9/1007* (2013.01); *C12N 15/52* (2013.01); *C12N 15/70* (2013.01); *C12P 13/02* (2013.01); *C12P 17/182* (2013.01); *C12R 2001/19* (2021.05)

(58) Field of Classification Search
None
See application file for complete search history.

(56) References Cited

PUBLICATIONS

Menendez-Perdomo and Peter Facchini. J. Biol. Chem. (2020) 295(6) pp. 1598-1612 (Year: 2020).*
Ming, et al. Genome Biology 2013, 14: R41, pp. 1-11 (Year: 2013).*
Morris, et al. Phytochemistry 170 (2020) 112193, pp. 1-11 (Year: 2020).*

* cited by examiner

*Primary Examiner* — Louise W Humphrey
*Assistant Examiner* — Jessica Faye Edwards
(74) *Attorney, Agent, or Firm* — WC&F IP (57) ABSTRACT

The present disclosure provides an O-methyltransferase protein with a highly specific catalytic function for multiple benzylisoquinoline alkaloids (BIAs) parent nuclei and an encoding gene and use thereof. Compared with wild-type O-methyltransferase, the O-methyltransferase protein (SEQ ID NO: 2) shows an enhanced enzymatic activity and a wider substrate scope. The O-methyltransferase protein can catalyze O-methylation of backbones from three BIAs, including monobenzylisoquinolines (norcoclaurine, coclaurine, and N-methylcoclaurine), aporphines (asimilobine and N-methylasimilobine), and protoberberines (scoulerine and tetrahydrocolumbamine). Meanwhile, this O-methyltransferase protein is highly regioselective for each backbone. The O-methyltransferase protein catalyzes methylation of the monobenzylisoquinolines at 6-OH and 7-OH, is only active on 6-OH of the backbone of the aporphines, and mainly catalyzes methylation of the protoberberines at 2-OH. Moreover, the O-methyltransferase protein has a stronger catalytic activity and can be used as a biocatalyst for the semi-synthesis of related compounds.

6 Claims, 6 Drawing Sheets
Specification includes a Sequence Listing.

SEQUENCE LISTING

```
Sequence total quantity: 4
SEQ ID NO: 1            moltype = DNA  length = 1095
FEATURE                 Location/Qualifiers
source                  1..1095
                        mol_type = other DNA
                        note = Nucleotides sequence of NnOMT6N323A
                        organism = synthetic construct
SEQUENCE: 1
atgggttcga ccaagaccca gatcaaaatt gcagaccaag aagaggagga agcttgcaac    60
tacgccatgc aattggccag cgcttcggtc gtacccatgg tattgaaagc agccatcgag   120
ctagatgtac tggagatcat tgctgaagca ggcgctgggg ctcacatctc gacctctgag   180
atcgcctctc atcttcctac gcagaaccca gatgcacctg ttatgctcga ccgtatgctg   240
cgtctcctag ccagcttctc cattcttact tgctccctac gcacccacga cgatggacgg   300
gtagagagac tctacggcct tgcacccgtg tgtaagttct tggtgaagaa cgaagatgga   360
gtgtcgatgg ctccactggt gctcatgaat caagacaagg tcctcatgga aagctggtac   420
catttgaaag acgcagtgct tgatggggga attccattta caaggccta cggcatgact    480
gcattcgaat accacggcac agacccccaga ttcaacaag tgttcaacag gggaatgtca   540
gatcactcca ccataaccat gaagaagatt cttgagacat acaagggatt cgagggcctc   600
aactccgtgg tggacgtcgg tgggggaact ggagctacac ttaacatgat tatttccaag   660
tacccttcca tcaagggcat taacttcgat ttgcctcacg ttattgaaga tgccccatcc   720
tatcctggcg tggagcatgt tggaggagat atgtttgtta gtgtacctaa aggagatgcc   780
atttcatga aatggatatg tcatgactgg agcgatgcac attgcttgga attttgaag    840
aactgctacc aagcgttacc ggaaaatgga aagataattg tcgtcgagtc cattcttccg   900
gtagctcccg agactaatct ttccgccaac ggtgtgttcc aacttgacaa catcatgctg   960
gcacatgcac ctggaggaaa agagagagcc gagaaagact ttgaggcctt ggccaagggc  1020
gccggattcg ctggagttgg agttatgtgt cgcgctttca acagctatgt catggaattc  1080
tataaatctg cttga                                                   1095

SEQ ID NO: 2            moltype = AA  length = 364
FEATURE                 Location/Qualifiers
source                  1..364
                        mol_type = protein
                        note = Amino acid sequence of O-methyltransferase protein
                        organism = synthetic construct
SEQUENCE: 2
MGSTKTQIKI ADQEEEEACN YAMQLASASV VPMVLKAAIE LDVLEIIAEA GAGAHISTSE    60
IASHLPTQNP DAPVMLDRML RLLASFSILT CSLRTHDDGR VERLYGLAPV CKFLVKNEDG   120
VSMAPLVLMN QDKVLMESWY HLKDAVLDGG IPFNKAYGMT AFEYHGTDPR FNKVFNRGMS   180
DHSTITMKKI LETYKGFEGL NSVVDVGGGT GATLNMIISK YPSIKGINFD LPHVIEDAPS   240
YPGVEHVGGD MFVSVPKGDA IFMKWICHDW SDAHCLEFLK NCYQALPENG KIIVVESILP   300
VAPETNLSAN GVFQLDNIML AHAPGGKERA EKDFEALAKG AGFAGVGVMC RAFNSYVMEF   360
YKSA                                                               364

SEQ ID NO: 3            moltype = DNA  length = 35
FEATURE                 Location/Qualifiers
source                  1..35
                        mol_type = other DNA
                        note = Primer-F
                        organism = synthetic construct
SEQUENCE: 3
gctggcacat gcacctggag gaaaagagag agccg                              35

SEQ ID NO: 4            moltype = DNA  length = 37
FEATURE                 Location/Qualifiers
source                  1..37
```

```
                    mol_type = other DNA
                    note = Primer-R
                    organism = synthetic construct
SEQUENCE: 4
ttcctccagg tgcatgtgcc agcatgatgt tgtcaag                                37
```

O-METHYLTRANSFERASE PROTEIN WITH HIGHLY SPECIFIC CATALYTIC FUNCTION FOR MULTIPLE BIAS PARENT NUCLEI AND ENCODING GENE AND USE THEREOF

CROSS REFERENCE TO RELATED APPLICATION

This patent application claims the benefit and priority of Chinese Patent Application No. 202210957619.6, filed with the China National Intellectual Property Administration on Aug. 10, 2022, the disclosure of which is incorporated by reference herein in its entirety as part of the present application.

REFERENCE TO SEQUENCE LISTING

A computer readable xml file entitled "15850008AA_SequenceListing.xml", that was created on Oct. 11, 2023, with a file size of about 6,540 bytes, contains the sequence listing for this application, has been filed with this application, and is hereby incorporated by reference in its entirety.

TECHNICAL FIELD

The present disclosure relates to the field of biotechnology, in particular to an O-methyltransferase protein with a highly specific catalytic function for multiple benzylisoquinoline alkaloids (BIAs) parent nuclei parent nuclei and an encoding gene and use thereof.

BACKGROUND

Benzylisoquinoline alkaloid (BIA) derivatives are a class of compounds that include analgesics such as morphine and codeine. Most of these compounds are synthesized from tyrosine in various plants via BIAs such as tetrahydropapaveroline (THP), norcoclaurine, and reticuline. The BIA and its derivatives have always been mainly extracted from plants. In view of this, there is an urgent need to explore chemical synthesis methods for such compounds.

SUMMARY

An objective of the present disclosure is to provide an O-methyltransferase protein with a highly specific catalytic function for multiple benzylisoquinoline alkaloids (BIAs) parent nuclei and an encoding gene and use thereof.

To achieve the above objective of the present disclosure, a first aspect of the present disclosure is to provide an O-methyltransferase protein with a highly specific catalytic function for multiple BIAs parent nuclei, where the O-methyltransferase protein includes a mutation (SEQ ID NO: 2) from N to A at amino acid 323 of O-methyltransferase.

The O-methyltransferase is from *Nelumbo nucifera*, and has a reference sequence number of XP_010241050.1 on the National Center of Biotechnology Information (NCBI).

A second aspect of the present disclosure is to provide a gene encoding the O-methyltransferase protein with a highly specific catalytic function for multiple BIA parent nuclei.

A third aspect of the present disclosure is to provide a biological material including the gene, where the biological material includes but is not limited to a recombinant DNA, an expression cassette, a transposon, a plasmid vector, a viral vector, and an engineered bacterium.

A fourth aspect of the present disclosure is to provide a recombinant microorganism, where the recombinant microorganism is constructed by introducing the gene encoding the O-methyltransferase protein into a microorganism (such as *Escherichia coli*) through a plasmid, or integrating the gene encoding the O-methyltransferase protein into a chromosome of the microorganism by means of genetic engineering.

A fifth aspect of the present disclosure is to provide use of the O-methyltransferase protein, the gene, the biological material, or the recombinant microorganism in any one of the following aspects:
1) preparation of a product with an O-methyltransferase activity; and
2) catalysis of O-methylation of a benzylisoquinoline compound.

Further, the benzylisoquinoline compound includes norcoclaurine, coclaurine, N-methylCoclaurine, asimilobine, N-methlyasimilobine, scoulerine, and tetrahydrocolumbamine.

By means of the above technical solutions, the present disclosure has at least the following advantages and beneficial effects:

(1) In the present disclosure, compared with wild-type O-methyltransferase, the O-methyltransferase protein with a highly specific catalytic function for multiple BIAs parent nuclei has an enhanced activity and a wider substrate range.

(2) The O-methyltransferase protein can catalyze monobenzylisoquinoline such as norcoclaurine to generate coclaurine and N-norarmepavine via a continuous catalytic reaction at 6-OH and 7-OH, can catalyze the coclaurine to generate the N-norarmepavine, and can catalyze N-methylcoclaurine to generate armepavine.

(3) The O-methyltransferase protein can also catalyze a backbone of aporphine such as asimilobine at 6-OH to generate N-nornuciferine, and catalyze N-methylasimilobine at 6-OH to generate nuciferine.

(4) The O-methyltransferase protein can catalyze methylation of a protoberberine substrate scoulerine at 2-OH to generate tetrahydropalmatrubine, and further generate a small amount of tetrahydropalmatine through methylation at 9-OH, and can also catalyze methylation of tetrahydrocolumbamine at 2-OH to generate the tetrahydropalmatine.

(5) The O-methyltransferase protein has a strong catalytic activity (greater than 40%) for the above seven substrates, and can be used as a biocatalyst for the semi-synthesis of corresponding products.

BRIEF DESCRIPTION OF THE DRAWINGS

FIGS. 2A-B show catalytic activity of $NnOMT6_{N323A}$ in a preferred example of the present disclosure to different substrates; where

FIGS. 3A-B show mass spectrograms of methylation of different substrates catalyzed by the $NnOMT6_{N323A}$ in a preferred example of the present disclosure; where

DETAILED DESCRIPTION OF THE EMBODIMENTS

The following examples are intended to illustrate the present disclosure, but not to limit the scope of the present disclosure. Unless otherwise specified, the examples each are in accordance with conventional experimental conditions, such as a molecular cloning laboratory manual of Sambrook et al. (Sambrook J & Russell D W, Molecular Cloning: a Laboratory Manual, 2001), or in accordance with conditions suggested by the manufacturer's instructions.

EXAMPLE 1

Cloning of Mutant Gene

NnOMT6$_{N323A}$ was a mutant of a gene NnOMT6 with an O-methylation function discovered for the first time in the present disclosure. The asparagine (N) at position 323 of an amino acid sequence in this mutant was mutated into alanine (A), such that the mutant showed an enhanced activity and a wider substrate range. The NnOMT6$_{N323A}$ gene was obtained by using a pET28a-NnOMT6 plasmid preserved in the Genetic Analysis Laboratory of Active Components of Traditional Chinese Medicine of the Institute of Chinese Materia Medica, the Chinese Academy of Chinese Medical Sciences (CACMS) as a template (a gene with a sequence number of XP_010241050.1 in the NCBI was named NnOMT6; the gene was constructed into a pET28a vector by PCR amplification and homologous recombination using cDNA as a template to obtain the recombinant plasmid pET28a-NnOMT6) with a Fast MultiSite Mutagenesis System kit of TransGen Biotech through point mutation.

1. Primer Design

A primer was designed at a mutation site according to the kit instructions; the primer included a 5'-end overlapping region and a 3'-end extending region, and the mutation site was located in the overlapping region; the primers had a length of about 25 to 40 nucleotides. The sequence of primers were as shown in table 1.

TABLE 1

| PCR amplification primers for mutant fragments | |
|---|---|
| Primer name | Primer sequence (5'-3') |
| Primer-F | GCTGGCACATGCACCTGGAGGAAAAGAGAGAGCCG (SEQ ID NO: 3) |
| Primer-R | TTCCTCCAGGTGCATGTGCCAGCATGATGTTGTCA AG (SEQ ID NO: 4) |

2. Preparation of Mutant Fragments

The pET28a-NnOMT6 plasmid was used as a template, and the mutant fragments were amplified using a 2×TransStart Fly PCRSuperMix system of TransGen Biotech. A reaction system was prepared according to Table 2, and a PCR reaction program was run according to Table 3. An amplified PCR product obtained was detected by 1% agarose gel electrophoresis, and resulting bands had a size consistent with those of the target fragments; 1 μL of a DMT enzyme was added to 50 μL of the PCR product, mixed well, and incubated at 37° C. for 1 h. Gel recovery was conducted with an Axysen AxyPrep DNA Gel Recovery Kit.

TABLE 2

| PCR amplification system of mutant fragments | |
|---|---|
| Reagent | 50 μL reaction system |
| pET28a-NnOMT6 plasmid | About 10 ng |
| Primer-F (10 μm) | 1 μL |
| Primer-R (10 μm) | 1 μL |
| 2×TransStart FastPfu Fly PCR SuperMix | 25 μL |
| Nuclease-free Water | Supplementing to 50 μL |

TABLE 3

| PCR reaction program | | | |
|---|---|---|---|
| Step | Temperature (° C.) | Time (s) | Number of cycles |
| Step1 | 95 | 180 | 1 |
| Step2 | 95 | 20 | 35 |
|  | 58 | 20 |  |
|  | 72 | 60 |  |
| Step3 | 72 | 420 | 1 |

3. Assembly of Mutant Fragments

The amplified linear fragments were seamlessly connected using a special recombinase and the principle of homologous recombination to construct a mutant plasmid. An assembly system of the mutants was shown in Table 4. The prepared system was gently mixed and reacted at 50° C. for 15 min. After the reaction was complete, the centrifuge tube was cooled on ice.

TABLE 4

| Reaction system for mutant assembly | |
|---|---|
| Reagent | Reaction system |
| 2×Assembly Mix | 5 μL |
| Purified mutant fragments | About 100 ng |
| Nuclease-free Water | Supplementing to 10 μL |

4. Transformation of a Ligation Product

5 μL of the recombinant product was added to DMT competent cells just thawed, mixed well by flicking, allowed to stand on ice for 30 min, heat-shocked at 42° C. for 45 s, and then immediately allowed to stand on ice for 2 min. 250 μL of LB medium was added, and the cells were cultured at 200 rpm in a shaker at 37° C. for 1 h. An obtained bacterial solution was centrifuged in a centrifuge at 4,500 rpm for 2 min, 200 μL of a supernatant in an upper layer was discarded, and 100 μL of the bacterial solution in a lower layer was mixed well by pipetting, and then gently evenly coated on a solid LB medium containing Kana resistance with a spreader, and when a surface of the medium was air-dried, the culture dish was covered and sealed, and then incubated overnight in a 37° C. incubator.

5. Screening and Sequencing of Positive Clones 3 colonies grown overnight were selected and placed in a 2 mL EP tube, added with 1 mL of a liquid LB medium containing Kana, cultured overnight by shaking at 37° C. and 200 rpm in a shaker, and an obtained bacterial solution was sent for sequencing. Sequencing results showed that the constructed mutant plasmid was completely consistent with the target sequence.

The NnOMT6$_{N323A}$ had 1,095 nucleotides (SEQ ID NO: 1) and encoded a protein of 364 amino acids (SEQ ID NO: 2).

6. Verification of Gene Function

The constructed pET28a-NnOMT6$_{N323A}$ vector with correct sequence verified by sequencing was transferred into a BL21(DE3) expression strain, and the gene function was verified by a prokaryotic expression system.

The induction, purification, enzyme activity analysis, and product identification of the recombinant protein were as follows:

(1) Induction of Recombinant Protein

The pET28a-NnOMT6$_{N323A}$ was placed in 3 mL of an LB broth (containing Kana 50 mg/L), and cultured overnight at 37° C. and 200 rpm.

A bacterial solution obtained from the overnight culture was transferred to 300 mL of a freshly sterilized LB broth (containing Kana 50 mg/L) and cultured on a shaker (200 rpm) at 37° C. until an OD$_{600}$ value was 0.6.

900 μL of isopropyl-β-D-thiogalactoside (IPTG, 100 mM) was added to 300 mL of the bacterial solution to a final concentration of 0.3 mM, and cultured at 16° C. and 180 rpm for not less than 16 h.

The bacterial solution was collected into a centrifuge tube, centrifuged at 4° C. and 8,000×g for 20 min, a supernatant was discarded, a bacterial pellet was collected, followed by conducting cell disruption.

(2) Purification of Recombinant Protein

The recombinant protein with an His tag in this experiment was purified by nickel column. Steps were as follows:

The bacterial pellet was resuspended in a loading buffer (50 mM NaH$_2$PO$_4$, 300 mM NaCl, and 10 mM imidazole), and the cells were disrupted with a low-temperature and ultra-high-pressure cell disruptor to release proteins, which were centrifuged at 4° C. and 10,000 rpm for 30 min, and a supernatant was collected for subsequent loading.

Figure 1:
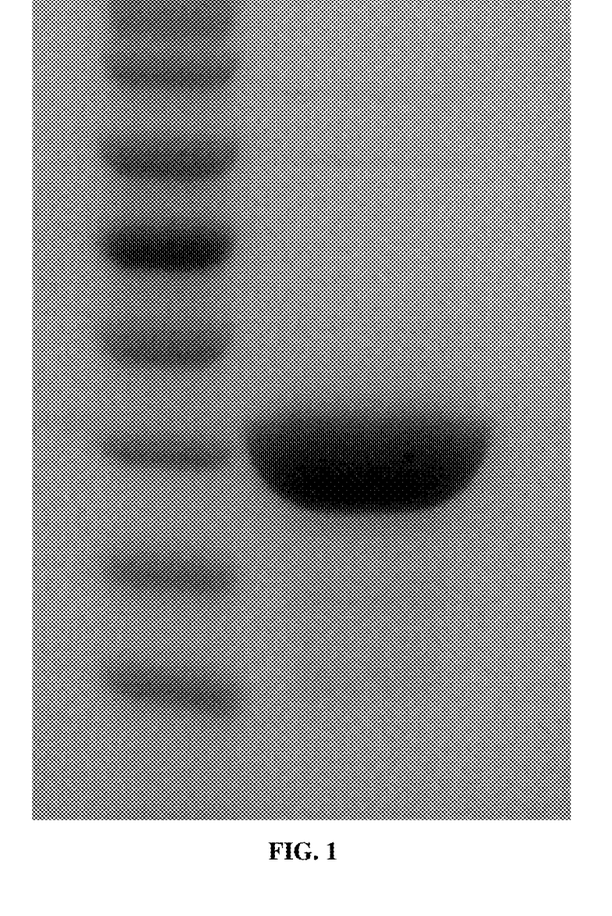
FIG. 1 shows a sodium dodecyl sulfate-polyacrylamide gel electrophoresis (SDS-PAGE) diagram of $NnOMT6_{N323A}$ recombinant protein in a preferred example of the present disclosure; where M represents a protein maker; and $NnOMT6_{N323A}$ represents a purified recombinant protein.

Assembly of a nickel column: Ni fillers (BeyoGold™ His-tag Purification Resin) were mixed well and added into a chromatographic column, a liquid outlet was opened, and ethanol was allowed to flow out naturally; 10 times a column volume of a loading buffer was added to equilibrate an affinity chromatographic column, a crude protein was added to the column, and after equilibrating for 5 min, a flow-through liquid was collected; the sample was passed through the column twice, after the sample has flowed through the filler of the affinity column, impurity proteins in the column were washed with 15 times a column volume of the loading buffer; the target protein was eluted with an eluent containing different concentrations of imidazole (20 mM, 50 mM, and 250 mM) separately, and a resulting eluate was collected. The purified protein was detected by SDS-PAGE. The results showed that the purified recombinant protein was largely enriched in the eluate containing 50 mM imidazole, and a target protein band was consistent with a predicted recombinant protein size (45.7 kDa). This indicated that the purified protein (with a purity of greater than 90%) could be further applied to later activity verification (FIG. 1).

(3) In Vitro Enzymatic Activity Test of NnOMT6$_{N323A}$

An in vitro enzymatic activity reaction was conducted at a pH value of 8.0 and 37° C. for 12 h in a 100 μL system containing 50 mM of a potassium phosphate buffer, 100 μM of a substrate, 200 μM of a SAM donor, and 50 μg of the purified protein. 100 μL of methanol was added to terminate the above reaction, the protein was centrifuged at 12,000×g for 30 min in a centrifuge, and a resulting supernatant was passed through a 0.22 μm microporous membrane and injected into UPLC-QTOF-MS/MS for detection. A sample prepared in a same way with boiled purified protein was served as a negative control.

The NnOMT6$_{N323A}$ was studied for substrate promiscuity with 15 benzylisoquinoline compounds (norcoclaurine (1), coclaurine (2), N-methylcoclaurine (3), norarmepavine (4), armepavine (5), lotusine (6), asimilobine (7), N-methylasimilobine (8), lirinidine (9), liensinine (10), isoliensinine (11), neferine (12), scoulerine (13), tetrahydrocolumbamine (14), and jatrorrhizine (15)).

The chromatographic conditions were as follows: a chromatographic column was an ACQUITY UPLC CSH C18 column (2.1 mm×50 mm, 1.7 μm). A mobile phase A was 0.1% formic acid water, and a mobile phase B was acetonitrile; gradient elution was conducted, including: 0-0.5 min, 2% B; 0.5-1 min, 2%-5% B; 1-5 min, 5%-9% B; 5-12 mM, 9%-10% B; 12-16 mM, 10%-15% B; 16-20 min, 15%-45% B; 20-22 min, 45% B-100% B. A sample injection volume was 2 μL, a column temperature was 35° C., and a flow rate was 0.3 mL/min.

The mass spectrometry conditions were as follows: an ion source was a Dusal ESI source; the substrate was detected in a positive ion (PI) mode with a scan range of m/z 100-1000. A sheath gas had a temperature of 350° C. and a flow rate of 11.0 L/min; a drying gas had a temperature of 350° C. and a flow rate of 8 L/min; an atomizer pressure was 45 psi; a capillary voltage was 4,000 V in PI mode and 3,500 V in NI mode; and a nozzle voltage was 500V in PI mode and 1,500 V in NI mode. MS/MS analysis was conducted with a collision energy of 30 eV and a collision energy voltage of 20 V.

Figure 2A:
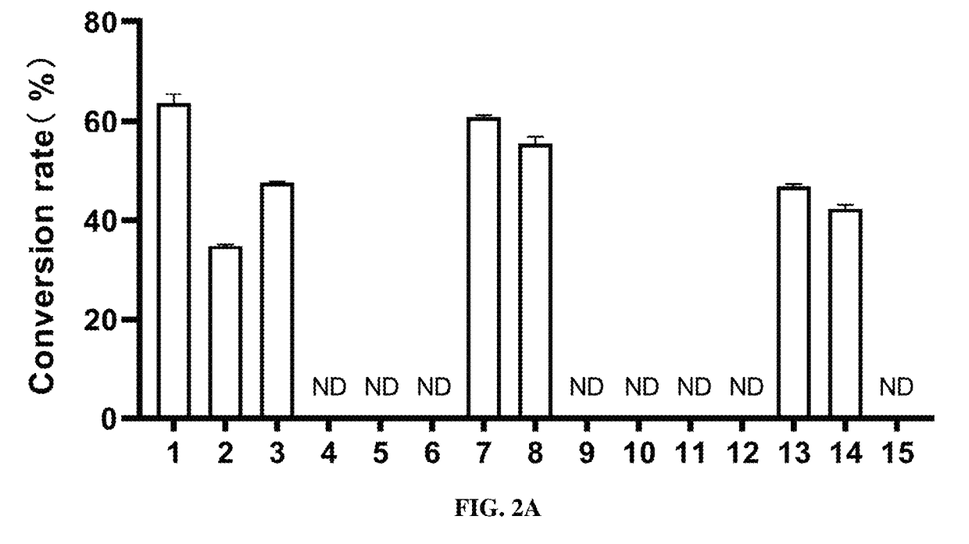
FIG. 2A represents a conversion rate of a methylation activity of $NnOMT6_{N323AO}$ to 15 substrates.
Figure 2B:
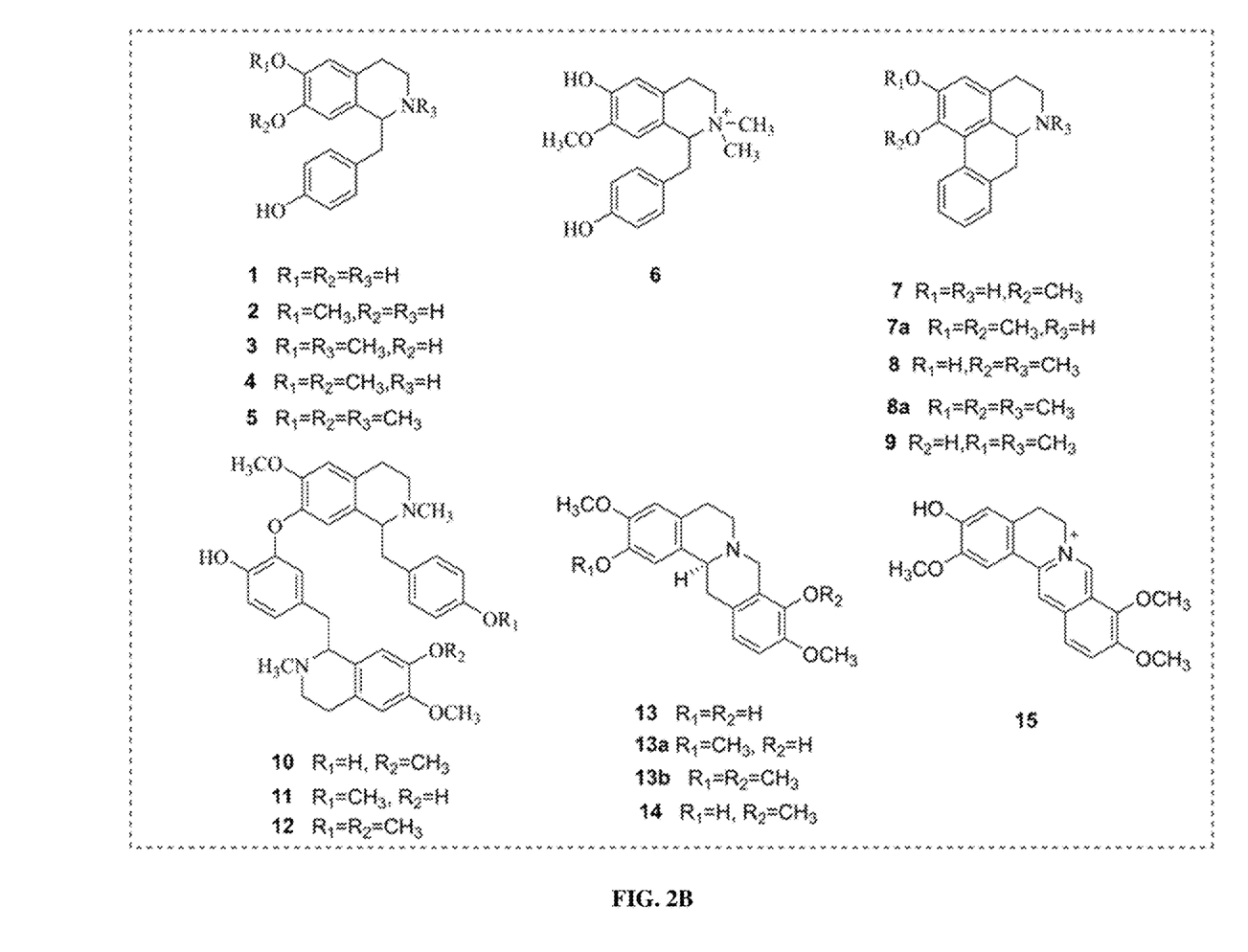
FIG. 2B represents structural diagrams of the 15 substrates.
Figure 3A:
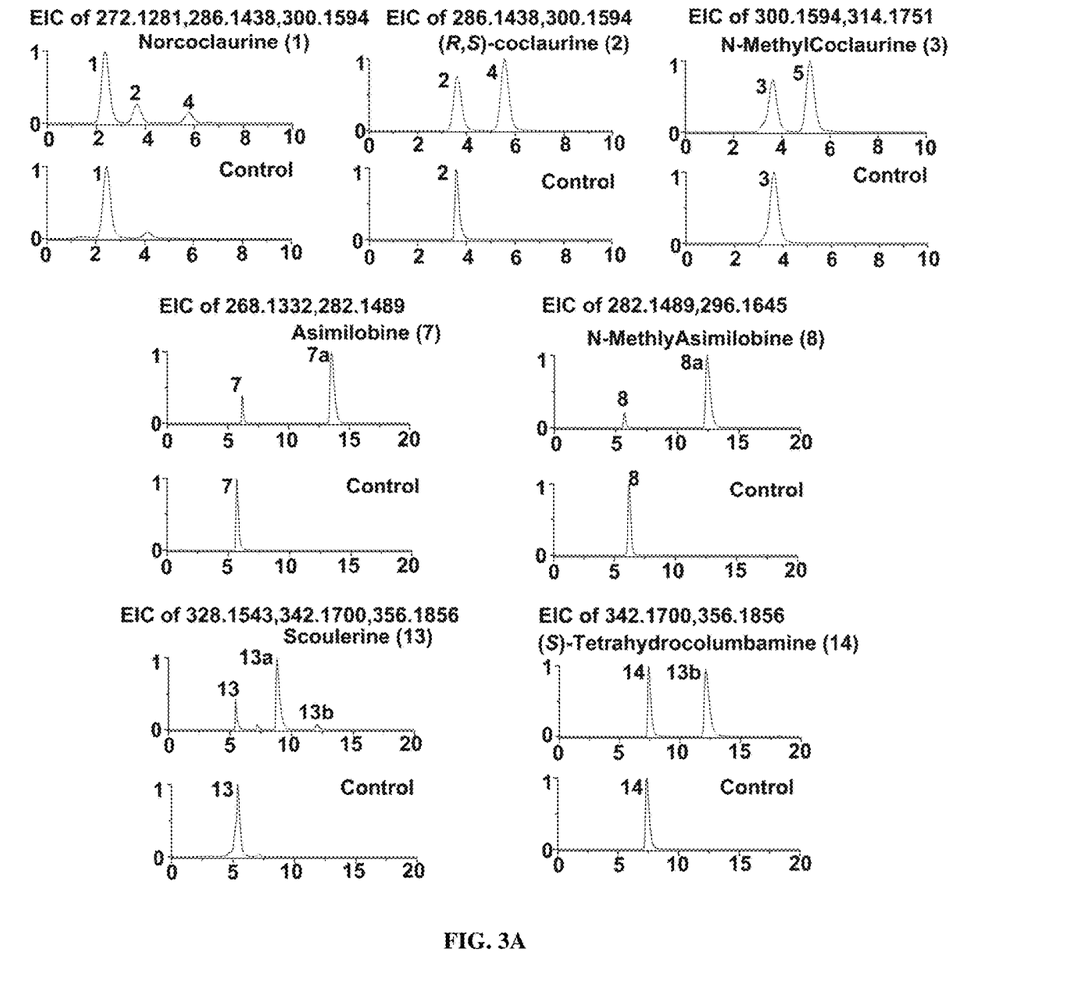
FIG. 3A represents an extracted ion chromatogram (EIC) of reaction substrate and product of compounds 1, 2, 3, 7, 8, 13, and 14 catalyzed by the NnOMT6$_{N323A}$.
Figure 3B:
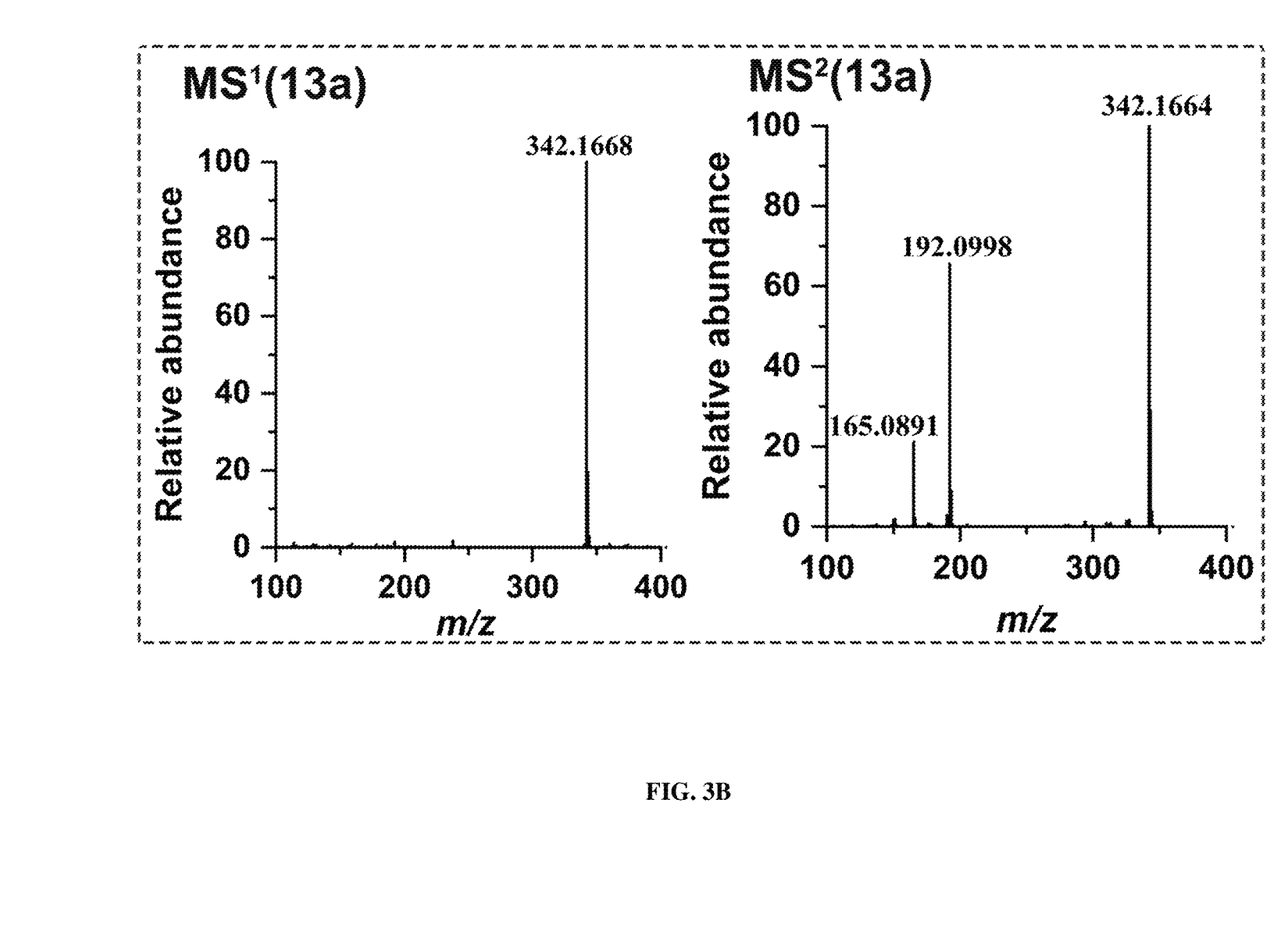
FIG. 3B represents MS and MS/MS patterns of a product 13a in a positive ion mode.

Experimental results showed that the NnOMT6$_{N323A}$ could catalyze the O-methylation of compounds 1, 2, 3, 7, 8, 13, and 14, but showed no activity on other substrates. A summary of the regioselectivity and specificity of NnOMT6$_{N323A}$ activity was shown in FIGS. 2A-B. For BIAs (1-6), the NnOMT6$_{N323A}$ could catalyze the O-methylation of norcoclaurine (1) at position 6 to generate compound 2, and then further catalyze the O-methylation of the compound 2 at position 7 to generate norarmepavine (4); this protein could also catalyze the O-methylation of N-methylcoclaurine(3) at position 7 to generate armepavine(5). The conversion rates of compounds 1, 2, and 3 were 63.7%, 34.8%, and 47.6%, respectively, indicating that a methylation activity of the phenolic hydroxyl group at the 6-position (1) was stronger than that at the 7-position (2). For the aporphine alkaloids (7-9) presented in *Nelumbo nucifera*, the protein had a catalytic activity on the compounds 7 and 8, catalyzed asimilobine (7) to generate N-nornuciferine (7a), and N-methlyasimilobine (8) to generate nuciferine (8a), with conversion rates of 60.8% and 55.4%, respectively. The protein had no catalytic activity on the compound 9, indicating that this protein could only catalyze the O-methylation of aporphine alkaloids at position 6. The NnOMT6$_{N323A}$ had no activity on bisbenzylisoquinoline alkaloids (10-12). For protoberberine compounds (13-15), the NnOMT6$_{N323A}$ could catalyze compound 13 to generate tetrahydropalmatrubine (13a). Compound 13 had only two methylation sites, and a retention time of the product was inconsistent with that of a reference substance 14. Therefore, the product was identified as tetrahydropalmatrubine (13a), and the 13a was further catalyzed by the NnOMT6$_{N323A}$ to generate tetrahydropalmatine (13b). The NnOMT6$_{N323A}$ could catalyze tetrahydrocolumbamine (14) to generate tetrahydropalmatine (13b) and had no activity on compound 15, indicating that the form of N-position showed an influence on the methylation activity. Except for 13a, the above reaction products were identified by comparison with the reference substance. The EICs of NnOMT6$_{N323A}$ in catalyzing the methylation of different substrates were shown in FIGS. 3A-B.

EXAMPLE 2

Figure 4:
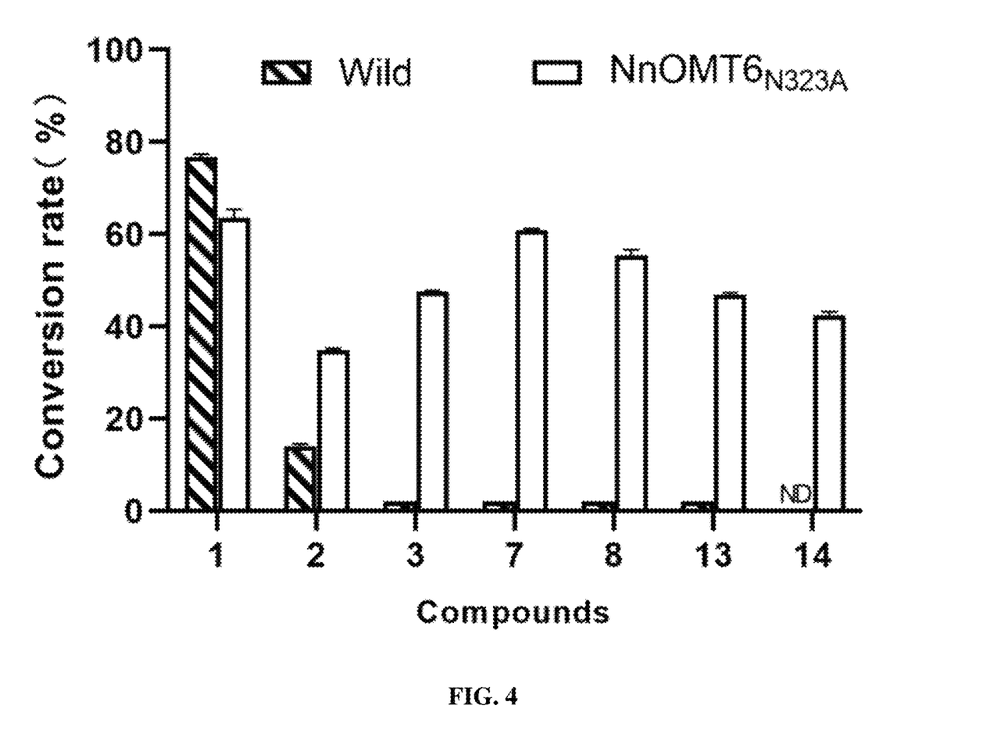
FIG. 4 shows a comparison of an enzymatic activity and a substrate spectrum of the mutant NnOMT6$_{N323A}$ and the wild-type O-methyltransferase in a preferred example of the present disclosure.

Comparison of an Enzymatic Activity and a Substrate Spectrum of the Mutant NnOMT6$_{N323A}$ and the Wild-Type O-methyltransferase As shown in FIG. 4, compared with the wild-type O-methyltransferase, the mutant NnOMT6$_{N323A}$ had a significantly enhanced catalytic activity for compound 2, by about two times. The wild-type O-methyltransferase had a catalytic conversion rate of less than 2% on compounds 3, 7, 8, and 13, showing only weak activity; while the mutant had an enhanced catalytic activity on these four compounds to 40% to 60%, and could be used as a biocatalyst for the semi-synthesis of corresponding products. The wild-type showed no catalytic activity on the substrate 14, while the mutant showed a conversion rate of about 42.3% on the substrate 14, thus increasing the broadness of substrate catalysis. A specific experimental method was the same as that in Example 1.

Although the present disclosure has been described in detail above with general description and specific embodiments, some modifications or improvements can be made on the basis of the present disclosure, which will be apparent to those skilled in the art. Therefore, all of these modifications or improvements made without departing from the spirit of the present disclosure fall within the claimed scope of the present disclosure.

What is claimed is:

1. An O-methyltransferase protein with a highly specific catalytic function for multiple benzylisoquinoline alkaloids (BIAs) parent nuclei, wherein the O-methyltransferase protein has an amino acid sequence as shown in SEQ ID NO: 2.

2. A gene encoding the O-methyltransferase protein with a highly specific catalytic function for multiple BIAs parent nuclei according to claim 1.

3. A biological material comprising the gene according to claim 2, wherein the biological material is selected from the group consisting of a recombinant DNA, an expression cassette, a transposon, a plasmid vector, a viral vector, and an engineered bacterium.

4. A recombinant microorganism, wherein the recombinant microorganism is constructed by introducing the gene encoding the O-methyltransferase protein according to claim 1 into a microorganism through a plasmid, or integrating the gene encoding the O-methyltransferase protein into a chromosome of the microorganism by means of genetic engineering.

5. The recombinant microorganism according to claim 4, wherein the microorganism is *Escherichia coli*.

6. A method for catalyzing O-methylation of a benzylisoquinoline compound with the O-methyltransferase protein according to claim 1, wherein the benzylisoquinoline compound is selected from the group consisting of norcoclaurine, coclaurine, N-methylCoclaurine, asimilobine, N-methylasimilobine, scoulerine, and tetrahydrocolumbamine.

* * * * *